US005217696A

United States Patent [19]

Wolverton et al.

[11] Patent Number: 5,217,696

[45] Date of Patent: Jun. 8, 1993

[54] COMBINED LAMP AND INDOOR AIR PURIFICATION APPARATUS

[76] Inventors: Billy C. Wolverton, 726 Pine Grove Rd.; John D. Wolverton, P.O. Box 411, both of Picayune, Miss. 39466

[21] Appl. No.: 832,479

[22] Filed: Feb. 7, 1992

[51] Int. Cl.[5] .............................................. A62B 11/00

[52] U.S. Cl. .................................... 422/121; 47/48.5; 47/66; 47/69; 47/79; 422/5; 422/120; 422/122

[58] Field of Search .................. 422/5, 121, 120, 122, 422/123, 305, 244; 47/69, 73, 79, 48.5, 2

[56] References Cited

U.S. PATENT DOCUMENTS

| | | | |
|---|---|---|---|
| 973,925 | 10/1910 | Downey | 47/79 |
| 2,228,892 | 1/1941 | Zimmerman | 47/79 |
| 2,300,776 | 11/1942 | Collins | 47/69 |
| 3,357,129 | 12/1967 | Torrence | 47/79 |
| 4,057,933 | 11/1977 | Enyeart | 47/79 |
| 4,732,591 | 3/1988 | Tujisawa et al. | 422/124 X |
| 4,975,251 | 4/1990 | Saceman | 422/124 |
| 5,078,972 | 1/1992 | Saceman | 422/124 |

OTHER PUBLICATIONS

Houseplants Indoor Air Pollutants and Allergic Reactions, B.C. Wolverton, NASA Technology Labs., MS 39529, Dec. 1986.

*Primary Examiner*—Robert J. Warden
*Assistant Examiner*—Amalia Santiago
*Attorney, Agent, or Firm*—Hugh E. Smith

[57] ABSTRACT

A lamp structure includes a base, with the base including an apertured periphery in communication with a support conduit chimney, with the support conduit chimney directed into a plant container, with the plant container further including a plurality of pneumatic feed conduits in pneumatic communication with the conduit chimney, and each feed conduit includes a matrix of apertures directed coextensively therethrough to direct air through a quantity of plant soil containing the pneumatic feed conduits for purification of the air as the air is by convection directed through the soil by an overlying lamp positioned within a reflective housing, with the reflective housing including a chimney coaxially aligned relative to the underlying plant container.

6 Claims, 4 Drawing Sheets

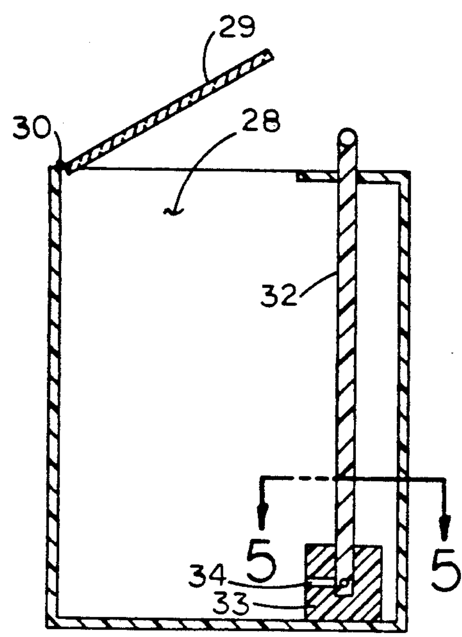
FIG. 4
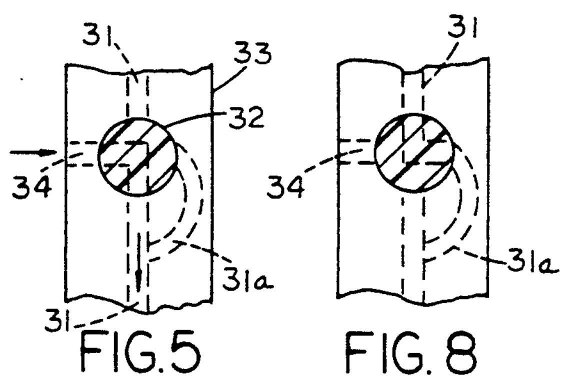
FIG. 5
FIG. 8
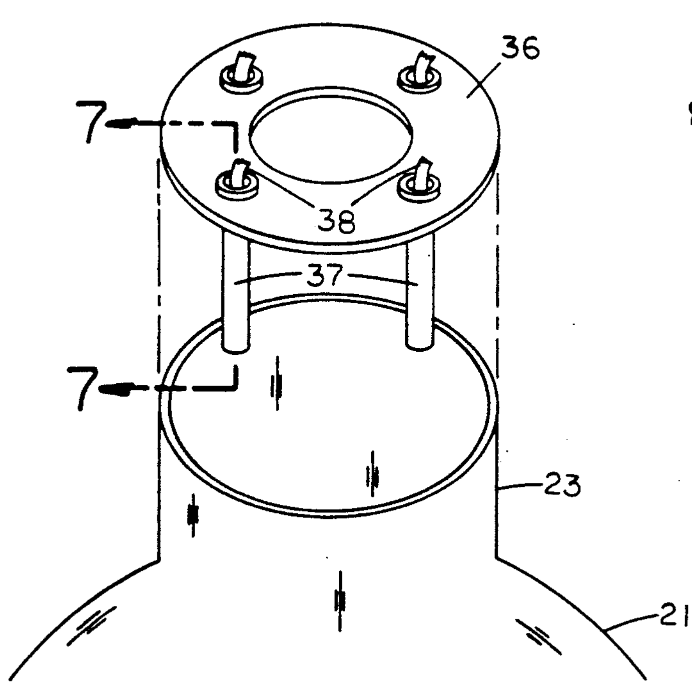
FIG. 6
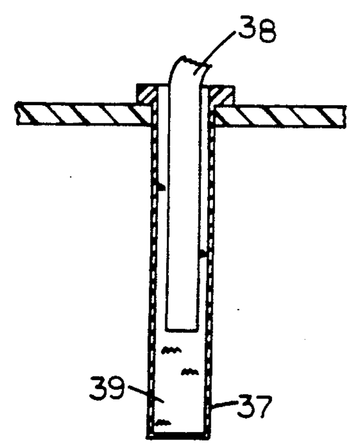
FIG. 7

COMBINED LAMP AND INDOOR AIR PURIFICATION APPARATUS

BACKGROUND OF THE INVENTION

1. Field of the Invention

The field of invention relates to air purification apparatus, and more particularly pertains to a new and improved combined lamp and indoor air purification apparatus wherein the same is directed to the purification of ambient air within an indoor environment.

2. Description of the Prior Art

The prior art has typically utilized various approaches to the cleansing air utilizing alternatively mechanical filters, mechanical filters utilizing absorbents, electronic air cleaners, ion generators, and plant/activated carbon air cleaners. Prior art utilize mechanical means of directing air through the associated filtration organization.

As soil contains an effective manner of degrading bacteria of various categories, as well as micro-organisms, the instant invention is directed to the effective manner of projecting ambient air through a soil quantity.

Prior art air purification devices are exemplified in U.S. Pat. No. 4,975,251 to Saceman wherein a room air purifier utilizes mechanical fan members to direct air into overlying soil.

U.S. Pat. No. 4,786,812 to Humphreys sets forth a germicidal ultra violet lamp for use as a germ killing device.

U.S. Pat. No. 4,845,602 to Lohecki sets forth a plant holder and light globe, wherein the globe is positioned medially of the plant holder to enhance heating of surrounding soil relative to the illumination bulb.

As such, it may be appreciated that there continues to be a need for a new and improved combined lamp and indoor air purification apparatus as set forth by the instant invention which addresses both the problems of ease of use as well as effectiveness in construction and in this respect, the present invention substantially fulfills this need.

SUMMARY OF THE INVENTION

In view of the foregoing disadvantages inherent in the known types of air purification apparatus now present in the prior art, the present invention provides a combined lamp and indoor air purification apparatus wherein convection currents are directed through a quantity of soil for purification of ambient air surrounding the apparatus of the instant invention. As such, the general purpose of the present invention, which well described subsequently in greater detail, is to provide a new and improved combined lamp and indoor air purification apparatus which has all the advantages of the prior art air purification apparatus and none of the disadvantages.

To attain this, the present invention provides a lamp structure including a base, with the base including an aperture periphery in communication with a support conduit chimney, with the support conduit chimney directed into a plant container, with the plant container further including a plurality of pneumatic feed conduits in pneumatic communication with the conduit chimney, and each feed conduit includes a matrix of apertures directed coextensively therethrough to direct air through a quantity of plant soil containing the pneumatic feed conduits for purification of the air as the air is by convection directed through the soil by an overlying lamp positioned within a reflective housing, with the reflective housing including a chimney coaxially aligned relative to the underlying plant container.

My invention resides not in any one of these features per se, but rather in the particular combination of all of them herein disclosed and claimed and it is distinguished from the prior art in this particular combination of all of its structures for the functions specified.

There has thus been outlined, rather broadly, the more important features of the invention in order that the detailed description thereof that follows may be better understood, and in order that the present contribution to the art may be better appreciated. There are, of course, additional features of the invention that will be described hereinafter and which the subject matter of the claims appended hereto. Those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved combined lamp and indoor air purification apparatus which has all the advantages of the prior art air purification apparatus and none of the disadvantages.

It is another object of the present invention to provide a new and improved combined lamp and indoor air purification apparatus which may be easily and efficiently manufactured and marketed.

It is a further object of the present invention to provide a new and improved combined lamp and indoor air purification apparatus which is of a durable and reliable construction.

An even further object of the present invention is to provide a new and improved combined lamp and indoor air purification apparatus which is susceptible of a low cost of manufacture with regard to both materials and labor, and which accordingly is then susceptible of low prices of sale to the consuming public, thereby making such combined lamp and indoor air purification apparatus economically available to the buying public.

Still yet another object of the present invention is to provide a new and improved combined lamp and indoor air purification apparatus which provides in the apparatuses and methods of the prior art some of the advantages thereof, while simultaneously overcoming some of the disadvantages normally associated therewith.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 4 is an orthographic view, taken along the lines 4—4 of FIG. 3 in the direction indicated by the arrows.

FIG. 5 is an orthographic view, taken along the lines 5—5 of FIG. 4 in the direction indicated by the arrows.

FIG. 6 is an isometric illustration of a modified chimney structure utilized by the invention.

FIG. 7 is an orthographic view, taken along the lines 7—7 of FIG. 6 in the direction indicated by the arrows.

FIG. 8 is an orthographic view of the FIG. 5—5 illustrating the valve in a closed orientation relative to a respective reservoir.

DESCRIPTION OF THE PREFERRED EMBODIMENT

Figure 1:
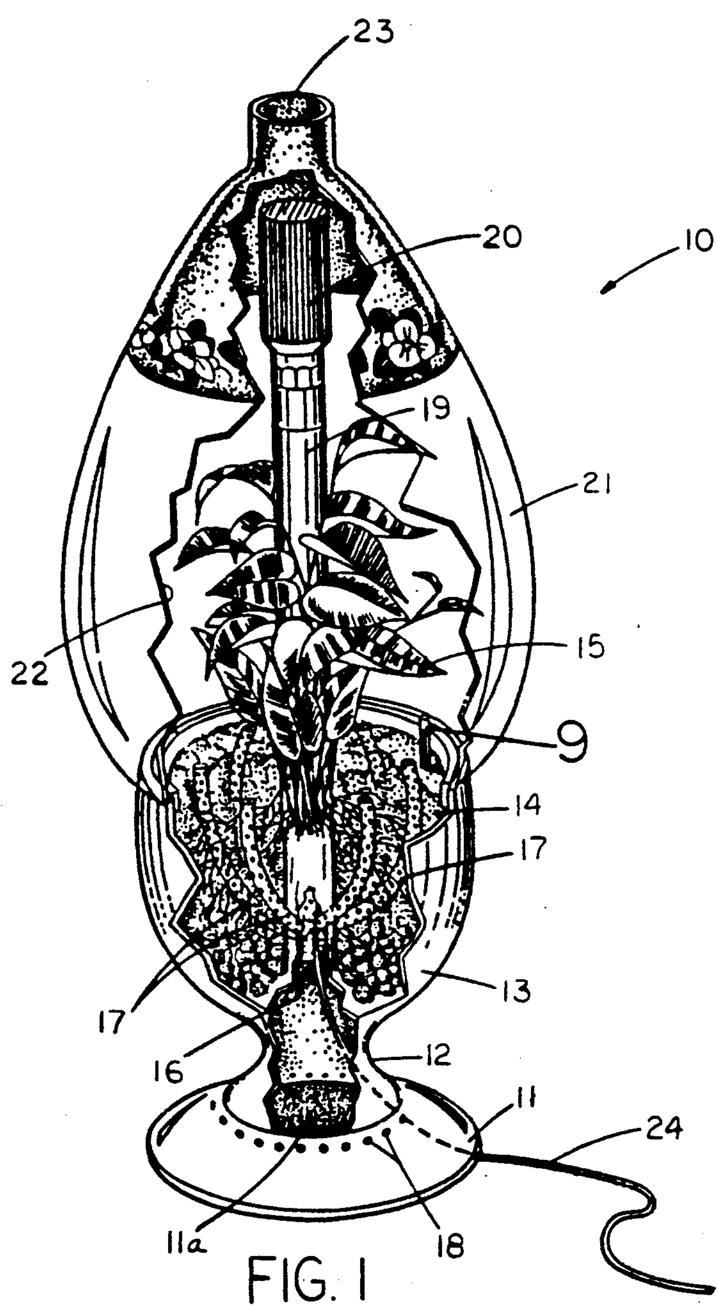
FIG. 1 is an isometric illustration of the instant invention.
Figure 9:
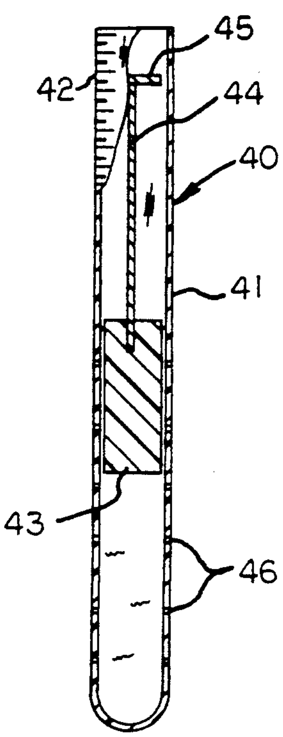
FIG. 9 is an orthographic cross-sectional illustration of the fluid level indicator members utilized by the apparatus.

With reference now to the drawings, and in particular to FIGS. 1 to 9 thereof, a new and improved combined lamp and indoor air purification apparatus embodying the principles and concepts of the present invention and generally designated by the reference numerals 10, 10*a*, and 10*b* will be described.

More specifically, the combined lamp and indoor air purification apparatus 10 of the invention essentially comprises a lamp structure to include a base plate 11, including a base plate floor 11*a*. A base plate support conduit 12 projects upwardly relative to the base plate in pneumatic communication with air feed ports 18 arranged through the base plate 11 above the floor 11*a*. The support conduit 12 is directed into a plant container 13 containing a predetermined quantity of soil 14 therewithin. The support conduit 12 is coaxially arranged relative to the plant container and the associated soil 14 supporting growth of a plant member 15. The support conduit 12 is directed into a support conduit chimney 16 coaxially of the container 13 in pneumatic communication with apertured pneumatic feed conduits 17 directed from the support conduit chimney 16 throughout the soil, with each feed conduit 17 including a matrix of apertures directed coextensively of the respective feed conduit 17 to enhance and under more effective the efficient transmission of greater volumes of air into the soil 14.

An illumination bulb support rod 19 extends coaxially of and upwardly of the container 13 fixedly mounted thereto and to the conduit chimney 16. The support, post 19 mounts an illumination bulb 20 at its upper distal end thereof. The illumination bulb effects radiant heating within a surrounding transparent housing 21 that extends coextensively from the plant container 13 upwardly in surrounding relationship relative to the illumination bulb 12 terminating in a housing chimney 23 coaxially aligned with and above the illumination bulb 20. It should be noted that the illumination bulb 20 may be further formed as ultra-violet type bulb in germicidal control of ambient air directed through the apparatus within the housing 21. The transparent housing 21 may be further formed with a reflective coating 22 coextensively about an interior surface of the transparent housing to enhance heat reflection, wherein such coatings are arranged not to interfere with light transmission through the transparent housing, and for the acceptance and accommodation of the apparatus, a design pattern may be directed about an upper portion of the transparent housing adjacent the housing chimney, as illustrated. Further, as is conventional, electrical conductive cable 24 is arranged to provide electrical energy to the illumination bulb through the illumination bulb support post 19.

It should be understood therefore that convection heating within the transparent housing 21 directs ambient air within an indoor environment through the air feed ports 18, the support conduit chimney 16, the feed conduit 17, and ultimately through the housing and exteriorly of the apparatus through the housing chimney 23. Further, noxious odors as well as various bacterial and germicidal contaminants within an ambient atmosphere, as well as out-gassing of various products utilized within an indoor environment are cleansed in their direction through the quantity of soil 14.

Figure 2:
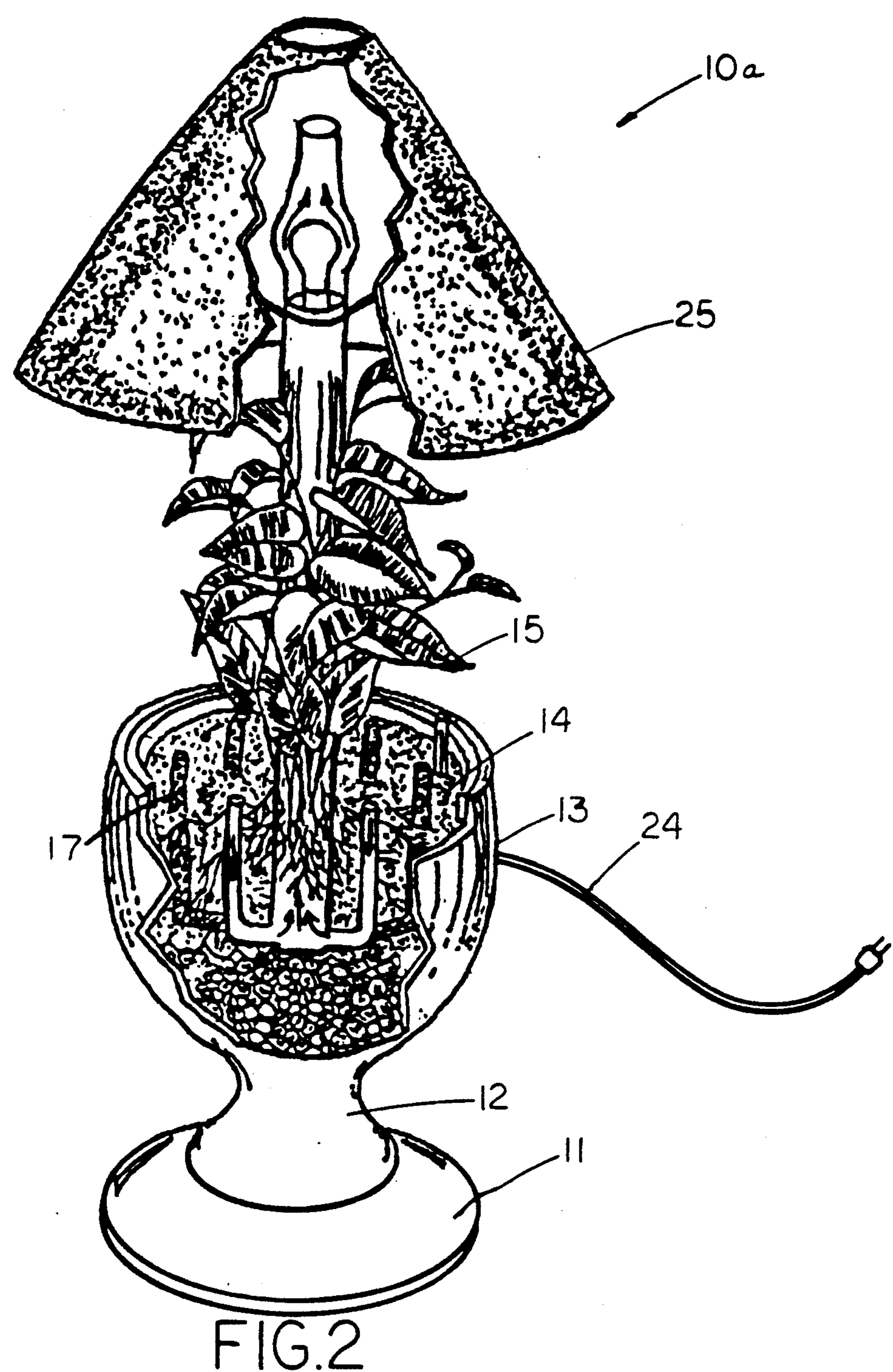
FIG. 2 is an isometric illustration of a modification of the invention.

The FIG. 2 setting forth the apparatus 10*a* includes an ultra-violet bulb 10*a* mounted within a reflective shade 25 formed of translucent material of a generally conical configuration terminating in an opened chimney at its upper distal end, where the reflective shade 25 is spaced above the container 14 as the ultra-violet bulb is thereby permitted access to a greater quantity of ambient air and as the shade still in its reflective qualities directs air through the base 11 and the soil 14 in a manner as described with reference to FIG. 1. The air flow directed into the central chimney is illustrated by arrow indication for purposes of illustration. This air flow in the FIG. 2 is effected at times by the shade 25 being spaced from the underlying container 13.

Figure 3:
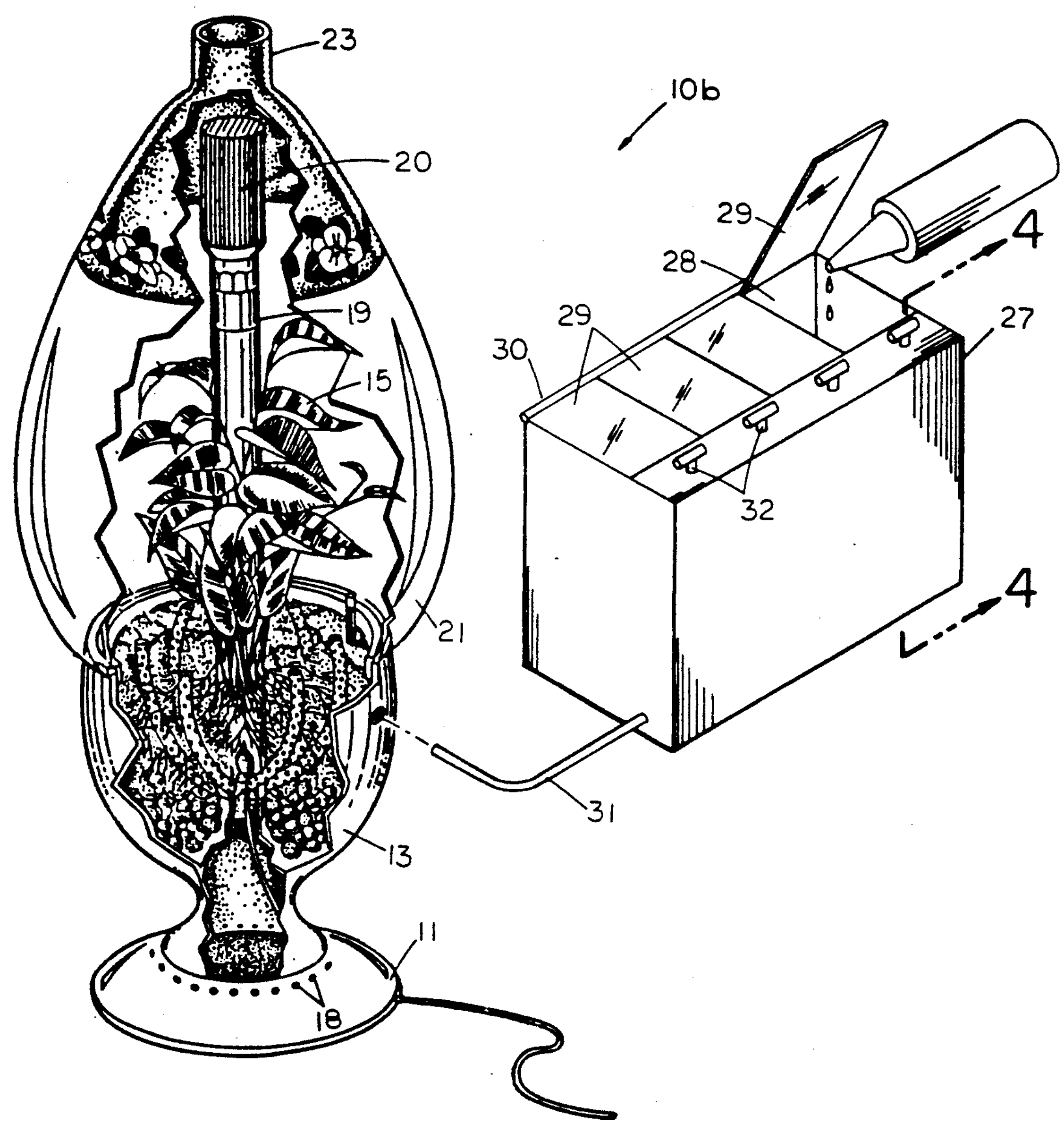
FIG. 3 is an isometric illustration of the invention of FIG. 1 to further include a watering apparatus.

The apparatus 10*b*, as illustrated in the FIG. 3 for example, further includes a fluid conduit 31 in communication with the soil 14 through a container 13 directed through a wall of the container. The fluid conduit 31 is in fluid communication with a fluid reservoir 27 and selectively with one or a plurality of fluid chambers 28 within the reservoir 27. Each fluid chamber 28 is arranged to receive a variously scented fluid as desired by individuals to enhance aromatic transmission of such fluids into an ambient environment. Each chamber 28 includes a lid 29 hingedly mounted about a hinge 30 relative to and overlying each chamber, with a chamber valve 32 associated with each fluid reservoir chamber 28. Each chamber valve 32 includes an "L" shaped valve conduit (see FIGS. 5 and 8) in selective communication with the fluid reservoir chamber 28 or direct such fluid into the fluid conduit 31 or upon rotation, bypassing an adjacent reservoir permitting contact with a bypass fluid conduit 31*a* to direct fluid along the fluid conduit 31 within the reservoir 27 from another source or chamber 28 within the reservoir construction 37. In this manner, one or a plurality of such fluid chambers 28 may direct their contents into the soil 14 for subsequent distribution into an ambient environment. The chamber valve 32, as illustrated, is rotatably mounted within a meter block 33 that includes a first conduit 34 in fluid communication with a chamber 28 and the fluid conduit 31, or selectively to utilize the bypass conduit 31*a* to bypass selectively each chamber as illustrated. The FIGS. 6 and 7 illustrate the additional use of a chimney plate 36 of a torroidal construction, including a plurality of fluid wells 37 orthogonally and downwardly extending relative to the chimney plate 36. The chimney plate is arranged for mounting to an upper terminal edge of the housing chimney 23 permitting heating of each fluid well that includes an aromatic fluid 39 contained therewithin and directing such fluid through a wick member 38 that is directed into the aromatic fluid projecting such aromatic fluid into an ambient environment in lieu of or in addition to the fluid reservoir structure 27.

The water lever indicator member that is positioned within the soil of the containers 13, as illustrated in the FIGS. 1, 2, and 3, employs a tubular member 41, including a graduated exterior wall surface 42 extending downwardly from an upper distal end of the tue 41. A float 43 is slidably mounted within the tube 41 and includes a float rod 44 formed with a "T" bar plate 45 at its upper distal end. The "T" bar plate 45 is arranged for association in viewing through the transparent tube 41 for operation with the indicia 42. The tube member 41 further includes a matrix of apertures 46 directed through the tube member to accommodate and receive fluid during a water replenishment procedure upon depositing water within the containers of the FIGS. 1 and 2.

As to the manner of usage and operation of the instant invention, the same should be apparent from the above disclosure, and accordingly no further discussion relative to the manner of usage and operation of the instant invention shall be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters patent of the United States is as follows:

1. A combined lamp and indoor air purification apparatus, comprising a plant container, a base plate, the base plate including a base plate floor and base plate support conduit extending upwardly of the base plate, with the base plate defining a base plate cavity between the base plate support conduit and the base plate floor, and a plurality of air feed ports formed and directed through the base plate in pneumatic communication with the cavity, and the base plate support conduit including an upper distal end, and the upper distal end fixedly mounted to a lower portion of said plant container, and the support conduit directed into a support conduit chimney positioned horizontally medially of the plant container, and the support conduit chimney including an illumination bulb support post extending upwardly of the support conduit chimney, with an illumination bulb mounted to an upper distal end of the support conduit chimney, and a housing extending upwardly from the plant container in surrounding relationship relative to the illumination bulb support post directed and extending above the illumination bulb support post, and a housing chimney positioned horizontally medially of the housing and vertically oriented relative to the underlying plant container, and a predetermined quantity of soil contained within the plant container.

2. An apparatus as set forth in claim 1 including a plurality of apertured pneumatic feed conduits in pneumatic communication with the support conduit chimney, with the feed conduits directed throughout the soil within the plant container, and the feed conduits each including a matrix of apertures directed coextensively of each feed conduit to direct air currents from the cavity into the soil.

3. An apparatus as set forth in claim 2 including a reflective coating adhered coextensively to an interior surface of the transparent housing.

4. An apparatus as set forth in claim 3 including a fluid reservoir, the fluid reservoir including at least one chamber, the chamber including a chamber lid hingedly mounted to the fluid reservoir above the at least one chamber, and a valve member in operative communication with the fluid chamber, and the valve member rotatably mounted within a meter block, the meter block including a first conduit in fluid communication with the fluid chamber, and the valve member including an "L" shaped valve conduit for selective communication with the first conduit, and a fluid conduit directed from the valve member to the plant container, and a plant container port receiving the fluid conduit to direct fluid from the fluid chamber selectively through the fluid conduit into the plant container.

5. An apparatus as set forth in claim 4 including a toroidal chimney plate arranged for reception upon an upper distal end of the housing chimney, and the torroidal chimney plate including a plurality of fluid wells orthogonally mounted to the chimney plate extending downwardly therefrom for reception within the housing chimney, each fluid well including an aromatic fluid contained therewithin, and a wick member directed into the aromatic fluid extending above each well.

6. An apparatus as set forth in claim 5 including a water indicator member tube positioned within the soil within the container, the tube projecting above the container, with the tube formed of a transparent material containing a float member slidably mounted therewithin, a float rod extending upwardly relative to the float member coaxially aligned within the tube and a "T" bar mounted at an upper distal end of the float rod, the tube including a series of indicia extending downwardly from an upper distal end of the tube cooperative with the "T" bar for indicating orientation of the "T" bar within the tube, the tube including a matrix of apertures directed through the tube extending from a lower distal end thereof to receive fluid therewithin permitting flotation of the float member within the tube.

* * * * *